United States Patent [19]

Date et al.

[11] Patent Number: 5,674,509
[45] Date of Patent: Oct. 7, 1997

[54] COSMETIC COMPOSITIONS

[75] Inventors: Robert Francis Date, Woking, United Kingdom; Elise Courpron, Paris, France; Zahid Nawaz, High Wycombe; Richard George A. Rolls, Bedfont, both of United Kingdom

[73] Assignee: The Procter & Gamble Company, Cincinnati, Ohio

[21] Appl. No.: 501,111

[22] PCT Filed: Feb. 1, 1994

[86] PCT No.: PCT/US94/01134

§ 371 Date: Aug. 9, 1995

§ 102(e) Date: Aug. 9, 1995

[87] PCT Pub. No.: WO94/17774

PCT Pub. Date: Aug. 18, 1994

[30] Foreign Application Priority Data

Feb. 9, 1993 [GB] United Kingdom ............ 9302518
Jun. 2, 1993 [GB] United Kingdom ............ 9311394

[51] Int. Cl.$^6$ .................. A61K 7/00; A61K 7/48
[52] U.S. Cl. .................. 424/401; 424/78.03; 424/70.12; 514/938
[58] Field of Search ................ 424/401, 70.12, 424/78.03, 70.16; 514/938

[56] References Cited

U.S. PATENT DOCUMENTS

| | | | |
|---|---|---|---|
| 3,919,430 | 11/1975 | Siegel | 424/365 |
| 4,776,976 | 10/1988 | Nakamura | 252/312 |
| 5,013,715 | 5/1991 | Mori et al. | 514/53 |
| 5,106,609 | 4/1992 | Bolich, Jr. et al. | 424/70 |

FOREIGN PATENT DOCUMENTS

| | | | |
|---|---|---|---|
| 0 541 830 | 5/1993 | European Pat. Off. | A61K 7/00 |
| 62 100 554 | 5/1987 | Japan . | |
| 05 032 789 | 2/1993 | Japan . | |
| 2 079 300 | 1/1982 | United Kingdom | C08L 83/04 |

Primary Examiner—Sallie M. Gardner
Attorney, Agent, or Firm—Anthony D. Sabatelli; David K. Dabbiere; T. David Reed

[57] ABSTRACT

A skin care composition in the form of an oil-in-water dispersion which comprises a silicone gum having a molecular weight of from about 200,000 to about 4,000,000 and wherein the composition additionally incorporates a fatty acid ester emulsifier based on a mixture of sorbitan acid ester and sucrose fatty acid ester. The composition provides improved moisturization, skin feel and skin care benefits and reduced greasiness, together with excellent rub-in and absorption characteristics.

2 Claims, No Drawings

COSMETIC COMPOSITIONS

This application is a 371 of PCT/US94/01134 filed Feb. 1, 1994.

TECHNICAL FIELD

The present invention relates to cosmetic compositions. In particular it relates to cosmetic compositions in the form of emulsions or lotions which provide improved moisturization, skin feel and skin care benefits and reduced greasiness, together with excellent rub-in and absorption characteristics. The compositions also display excellent stability characteristics at normal and elevated temperatures.

BACKGROUND OF THE INVENTION

Skin is made up of several layers of cells which coat and protect the keratin and collagen fibrous proteins that form the skeleton of its structure. The outermost of these layers, referred to as the stratum corneum, is known to be composed of 25 nm protein bundles surrounded by 8 nm thick layers. Anionic surfactants and organic solvents typically penetrate the stratum corneum membrane and, by delipidization (i.e. removal of the lipids from the stratum corneum), destroy its integrity. This destruction of the skin surface topography leads to a rough feel and may eventually permit the surfactant, or solvent to interact with the keratin, creating irritation.

It is now recognised that maintaining the proper water gradient across the stratum corneum is important to its functionality. Most of this water, which is sometimes considered to be the stratum corneum's plasticizer, comes from inside the body. If the humidity is too low, such as in a cold climate, insufficient water remains in the outer layers of the stratum corneum to properly plasticize the tissue, and the skin begins to scale and becomes itchy. Skin permeability is also decreased somewhat when there is inadequate water across the stratum corneum. On the other hand, too much water on the outside of the skin causes the stratum corneum to ultimately sorb three to five times its own weight of bound water. This swells and puckers the skin and results in approximately a two to three fold increase in the permeability of the skin to water and other polar molecules.

Thus, a need exists for compositions which will assist the stratum corneum in maintaining its barrier and water-retention functions at optimum performance in spite of deleterious interactions which the skin may encounter in washing, work, and recreation.

Conventional cosmetic cream and lotion compositions as described, for example, in Sagarin, Cosmetics Science and Technology, 2nd Edition, Vol. I, Wiley Interscience (1972) and Encyclopaedia of Chemical Technology, Third Edition, Volume 7 are known to provide varying degrees of emolliency, barrier and water-retention (moisturizing) benefits. However, they can also suffer serious negatives in terms of skin feel (i.e. they often feel very greasy on the skin) as well as having poor rub-in, absorption and residue characteristics.

The present invention therefore provides skin-care cosmetic compositions which provide improvements in moisturization, absorption, skin feel and skin care characteristics and which in particular provide improved short and longer term moisturizing effectiveness, while at the same time reducing stickiness and avoiding a greasy feel on the skin. The compositions also display excellent stability characteristics at both normal and elevated temperatures.

SUMMARY OF THE INVENTION

Accordingly, in one aspect of the present invention, there is provided a skin care composition in the form of an oil-in-water dispersion comprising one or more distinct oil phases, wherein the primary oil phase is present in a level of from about 4% to about 16% by weight and wherein the composition incorporates from about 2% to about 10% of an emulsifier capable of forming liquid crystals in water. Preferably, the emulsifier is a fatty acid ester blend based on a mixture of sorbitan fatty acid ester and sucrose fatty acid ester, and wherein the ratio of primary oil phase to fatty acid ester emulsifier is in the range from about 6:1 to about 1:1.

The compositions of this aspect of the present invention take the form of an oil-in-water emulsion or dispersion containing one or more distinct emulsified or dispersed oil phases and an essential emulsifier component as well as various optional ingredients as indicated below. All levels and ratios are by weight of total composition, unless otherwise indicated. Chain length and degrees of ethoxylation are also specified on a weight average basis.

According to the first aspect of the invention, a first essential component of the composition herein is an oil phase, referred to herein as a primary oil phase, which can comprise a single oily component or a mixture of oily components in miscible or homogeneous form. This is preferably present in 5% an amount of from about 4% to about 16%, more preferably from about to about 11% by weight of composition. The level of primary oil phase component is found to be important herein for achieving optimum moisturization and greasiness characteristics. The primary oil phase generally comprises a natural or synthetic oil selected from mineral, vegetable, and animal oils, fats and waxes, fatty acid esters, fatty alcohols, fatty acids and mixtures thereof having emollient cosmetic properties. The primary oil phase component is preferably essentially silicone-free, ie contains no more than about 10%, preferably no more than about 5% by weight of silicon-based materials. It will be understood that the oil phase may contain small levels (eg. up to about 25%, preferably 10%) of oil phase soluble emulsifier ingredients. Such ingredients are not to be considered as oil phase components from the viewpoint of determining the oil phase level and required HLB. In preferred embodiments, the overall required HLB of the oil phase is from about 8 to about 12, especially from about 9 to about 11, required HLB being determined by summing the individual required HLB values for each component of the oil phase multiplied by its W/W percentage in the oil phase (see ICI Literature on HLB system).

Suitable primary oil phase components for use herein include, for example, optionally hydroxy-substituted $C_8$–$C_{50}$ unsaturated fatty acids and esters thereof, $C_1$–$C_{24}$ esters of $C_8$–$C_{30}$ saturated fatty acids such as isopropyl myristate, cetyl palmirate and octyldodecylmyristate (Wickenol 142), beeswax, saturated and unsaturated fatty alcohols such as behenyl alcohol and cetyl alcohol, hydrocarbons such as mineral oils, petrolatum and squalane, fatty sorbitan esters (see U.S. Pat. No. 3988255, Selden, issued Oct. 26, 1976), lanolin and lanolin derivatives, animal and vegetable triglycerides such as almond oil, peanut oil, wheat germ oil, linseed oil, jojoba oil, oil of apricot pits, walnuts, palm nuts, pistachio nuts, sesame seeds, rapeseed, cads oil, corn oil, peach pit oil, poppyseed oil, pine oil, castor oil, soybean oil, avocado oil, safflower oil, coconut oil, hazelnut oil, olive oil, grapeseed oil, and sunflower seed oil and $C_1$–$C_{24}$ esters of dimer and trimer acids such as diisopropyl dimerate, diisostearylmalate, diisostearyldimerate and triisostearyltrimerate. Of the above, highly preferred are the mineral oils, petrolatums, unsaturated fatty acids and esters thereof and mixtures thereof.

Compositions herein preferably also comprise a secondary oil phase which in preferred embodiments is present in a level of from about 0.1% to about 20%, especially from about 1% to about 10% by weight of composition. Moreover, the primary oil phase is preferably present in weight excess of the secondary oil phase. The secondary oil phase component is preferably silicone-based. Suitable silicone components herein include water-insoluble silicones inclusive of non-volatile polyalkyl and polyaryl siloxane gums and fluids, volatile cyclic and linear polyalkylsiloxanes, polyalkoxylated silicones, amino and quaternary ammonium modified silicones, rigid cross-linked and reinforced silicones and mixtures thereof. In preferred embodiments the silicone component is a silicone gum having a molecular weight of from about 200,000 to about 4,000,000 or a mixture of silicones including the silicone gum. In mixtures, the silicone gum preferably constitutes from about 5% to about 40%, especially from about 10% to 20% by weight of the silicone mixture. The silicone or silicone mixture preferably constitutes from about 0.1% to about 20%, more preferably from about 0.5% to about 15%, and especially from about 1% to about 10% by weight of composition.

A preferred silicone component for use herein consists essentially of:

(i) a silicone having a molecular weight of from about 200,000 to about 4,000,000 selected from dimethiconol, fluorosilicone and dimethicone and mixtures thereof; and (ii) a silicone-based carrier having a viscosity from about 0.65 mm$^2$.s$^{-1}$ to about 100 mm$^2$.s$^{-1}$, wherein the ratio of i) to ii) is from about 10:90 to about 20:80 and wherein said silicone component has a final viscosity of from about 500 mm$^2$.s$^{-1}$ to about 10,000 mm$^2$.s$^{-1}$.

Dimethiconol-based silicones suitable for use herein have the chemical structure (II):

HO(CH$_3$)$_2$SiO[(CH$_3$)$_2$SiO]$_n$(CH$_3$)$_2$SiOH where n is from about 2000 to about 40,000, preferably from about 3000 to about 30,000.

The fluorosilicones useful herein have a molecular weight of from about 200,000 to about 300,000, preferably from about 240,000 to about 260,000 and most preferably about 250,000.

The silicone gums include dimethicones as described by Petrarch and others including U.S. Pat. No. 4,152,416, May 1, 1979 to Spitzer, et al, and Noll, Walter, *Chemistry and Technology of Silicones*. New York: Academic Press 1968. Also describing silicone gums are General Electric Silicone Rubber Product Data Sheets SE 30, SE 33, SE 54 and SE 76. "Silicone gum" materials useful herein denote high molecular weight materials having a mass-average molecular weight in excess of about 200,000 and preferably from about 200,000 to about 4,000,000. Typically, they have a viscosity at 25° C. in excess of about 1,000,000 mm$^2$.s$^{-1}$. Specific examples include polydimethylsiloxane, (polydimethylsiloxane) (methylvinylsiloxane) copolymer, poly(dimethylsiloxane) (diphenyl) (methylvinylsiloxane) copolymer and mixtures thereof.

The silicone-based carriers suitable for use herein include certain silicone fluids. The silicone fluid can be either a polyalkyl siloxane, a polyaryl siloxane, a polyalkylaryl siloxane or a polyether siloxane copolymer. Mixtures of these fluids can also be used and are preferred in certain executions.

The polyalkyl siloxane fluids that can be used include, for example, polydimethylsiloxanes with viscosities ranging from about 0.65 to 600,000 mm$^2$.s$^{-1}$, preferably from about 0.65 to about 10,000 mm$^2$.s$^{-1}$ at 25° C. These siloxanes are available, for example, from the General Electric Company as the Viscasil (RTM) series and from Dow Corning as the Dow Corning 200 series. The essentially non-volatile polyalkylarylsiloxane fluids that can be used include, for example, polymethylphenylsiloxanes, having viscosities of about 0.65 to 30,000 mm$^2$.s$^{-1}$ at 25° C. These siloxanes are available, for example, from the General Electric Company as SF 1075 methyl phenyl fluid or from Dow Corning as 556 Cosmetic Grade Fluid. Also suitable for use herein are certain volatile cyclic polydimethylsiloxanes having a ring structure incorporating from about 3 to about 7 (CH$_3$)$_2$SiO moieties.

The viscosity can be measured by means of a glass capillary viscometer as set forth in Dow Corning Corporate Test Method CTM0004, Jul. 29, 1970. Preferably the viscosity of the silicone blend constituting the secondary oil phase ranges from about 500 mm$^2$.s$^{-1}$ to about 100,000 mm$^2$.s$^{-1}$, preferably from about 1000 mm$^2$.s$^{-1}$ to about 10,000 mm$^2$.s$^{-1}$.

The most preferred silicone component for use herein is a dimethiconol gum having a molecular weight of from about 200,000 to about 4,000,000 along with a silicone carrier with a viscosity of about 0.65 to 100 mm$^2$.s$^{-1}$. An example of this silicone component is Dow Corning Q2-1403 (85% 5 mm$^2$.s$^{-1}$ Dimethicone Fluid/15% Dimethiconol) and Dow Corning Q2-1401 available from Dow Corning.

Another class of silicone component suitable for use herein include polydiorganosiloxane-polyoxyalkylene copolymers containing at least one polydiorganosiloxane segment and at least one polyoxyalkylene segment, said polydiorganosiloxane segment consisting essentially of $R_b SiO_{(4-b)/2}$ siloxane units wherein b has a value of from about 0 to about 3, inclusive, there being an average value of approximately 2 R radicals per silicon for all siloxane units in the copolymer, and R denotes a radical selected from methyl, ethyl, vinyl, phenyl and a divalent radical bonding said polyoxyalkylene segment to the polydiorganosiloxane segment, at least about 95% of all R radicals being methyl; and said polyoxyalkylene segment having an average molecular weight of at least about 1000 and consisting of from about 0 to about 50 mol percent polyoxypropylene units and from about 50 to about 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical; the weight ratio of polydiorganosiloxane segments to polyoxyalkylene segments in said copolymer having a value of from about 2 to about 8. Such polymers are described in U.S. Pat. No. 4,268,499.

Preference for use herein are polydiorganosiloxane-polyoxyalkylene copolymers having the general formula:

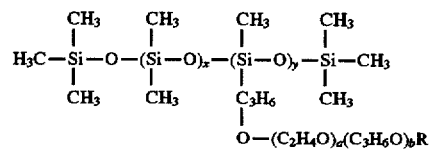

wherein x and y are selected such that the weight ratio of polydiorgano-siloxane segments to polyoxalkalkylene segments is from about 2 to about 8, the mol ratio of a:(a+b) is from about 0.5 to about 1, and R is a chain terminating group, especially selected from hydrogen; hydroxyl; alkyl, such as methyl, ethyl, propyl, butyl, benzyl; aryl, such as phenyl; alkoxy such as methoxy, ethoxy, propoxy, butoxy; benzyloxy; aryloxy, such as phenoxy; alkynyloxy, such as vinyloxy and allyloxy; acyloxy, such as acetoxy, acryloxy and propionoxy and amino, such as dimethylamino.

The number of and average molecular weights of the segments in the copolymer are such that the weight ratio of polydiorganosiloxane segments to polyoxyalkylene segments in the copolymer is preferably from about 2.5 to about 4.0.

Suitable copolymers are available commercially under the tradenames Belsil (RTM) from Wacker-Chemie GmbH, Geschäftsbereich S, Postfach D-8000 Munich 22 and Abil (RTM) from Th. Goldschmidt Ltd., Tego House, Victoria Road, Ruislip, Middlesex, HA40YL. Particularly preferred for use herein are Belsil (RTM) 6031 and Abil (RTM) B88183.

The above polydiorganosiloxane—polyoxyalkylene copolymers can be used above or in admixture with other silicones, for example, the volatile cyclic polydimethylsiloxanes. Moreover, such copolymers and mixtures can be used in combination with the herein defined silicone gums.

The silicone component is valuable herein in conjunction with the liquid-crystal forming emulsifier for modifying the perceived skin feel of the composition. Highly preferred in this respect are silicone gums having a molecular weight of from 200,000 to 4,000,000. Thus according to another aspect of the invention, there is provided a skin care composition in the form of an oil-in-water dispersion which comprises a silicone or mixture of silicones in a level of from 0.1% to 20% by weight, the silicone or silicone mixture comprising a silicone gum having a molecular weight of from about 200,000 to about 4,000,000 and wherein the composition additionally incorporates from about 2% to about 10% of an emulsifier capable of forming liquid crystals in water, the emulsifier being a fatty acid ester blend based on a mixture of sorbitan fatty acid ester and sucrose fatty acid ester. The fatty acid ester in each instance is preferably $C_8-C_{24}$, more preferably $C_{10}-C_{20}$. The silicone or silicone mixture is preferably present in a level of from about 0.5% to about 15%, preferably from 1% to about 10% by weight of composition, this level being based on the total blend of gum and non-gum silicone materials. In preferred embodiments, the compositions of this aspect of the invention comprise a primary oil phase which is essentially silicone-free together with a secondary oil phase comprising the silicone gum. The primary oil phase is described in detail above.

Preferred embodiments herein comprise from about 0.1% to about 10% by weight of an unsaturated fatty acid or ester. Preferred unsaturated fatty acids and esters for use herein are optionally hydroxy substituted $C_8-C_{50}$ unsaturated fatty acids and esters, especially esters of ricinoleic acid. The unsaturated fatty acid or ester component is valuable herein in combination with the liquid crystal forming emulsifier for improving the skin feel and rub-in characteristics of the compositon. Highly preferred in this respect is cetyl ricinoleate.

Thus according to another aspect of the invention, there is provided a skin-care composition in the form of an oil-in-water dispersion wherein the composition incorporates from about 2% to about 10% by weight of an emulsifier capable of forming liquid crystals in water, the emulsifier being a fatty acid ester blend based on a mixture of sorbitan fatty acid ester and sucrose fatty acid ester, and wherein the composition additionally incorporates from about 0.1% to about 10% of an optionally hydroxy substituted $C_8-C_{50}$ unsaturated fatty acid or an ester thereof, preferably an ester of ricinoleic acid.

A second essential ingredient in the composition herein is an emulsifier capable of forming liquid crystals in water, for example, at ambient or elevated temperatures. Preferably the emulsifier is capable of forming liquid crystals (especially smectic lyotropic liquid crystals) at a temperature in the range from about 20° C. to about 80° C. and in particular when the emulsifier is incorporated in product or when the product is applied to the skin. The emulsifier is preferably incorporated into the composition in an amount of from about 2% to about 10%, preferably from about 3% to about 7% by weight of composition. The emulsifier preferred for use herein is a fatty acid ester blend based on a mixture of sorbitan or sorbitol fatty acid ester and sucrose fatty acid ester, the fatty acid in each instance being preferably $C_8-C_{24}$, more preferably $C_{10}-C_{20}$. The preferred fatty acid ester emulsifier from the viewpoint of moisturisation is a blend of sorbitan or sorbitol $C_{16}-C_{20}$ fatty acid ester with sucrose $C_{10}-C_{16}$ fatty acid ester, especially sorbitan stearate and sucrose cocoate. This is commercially available from ICI under the trade name Ariatone 2121. The stabilisation mechanism of formulation derived from Ariatone 2121 is based on the formation of distinct liquid crystalline structures in the water phase into which the oil phase is dispersed. In order to achieve optimum moisturisation, absorption and skin feel together with reduced greasiness it is desirable for the ratio of primary oil to fatty acid ester emulsifier to lie in the range from about 6:1 to about 1:1, preferably from about 4:1 to about 1:1.

A wide variety of optional ingredients such as nonocclusive moisturizers, humectants, gelling agents, neutralizing agents, perfumes, colouring agents and surfactants, can be added to the skin compositions herein.

The compositions herein can comprise a humectant. Suitable humectants for use herein include sorbitol, propylene glycol, butylene glycol, hexylene glycol, ethoxylated glucose derivatives, hexanetriol, glycerine, water-soluble polyglycerylmethacrylate lubricants and panthenols. A preferred humectant herein is glycerine (sometimes known as glycerol or glycerin). Chemically, glycerine is 1,2,3-propanetriol and is a product of commerce. One large source of the material is in the manufacture of soap. Also preferred for use herein is butylene glycol.

In the present compositions, the humectant is preferably present at a level of from about 0.1% to about 20%, more preferably from about 1% to about 10%, and especially from about 2% to about 5% by weight of composition.

Suitable polyglycerylmethacrylate lubricants for use in the compositions of this invention are available under the trademark Lubrajel (RTM) from Guardian Chemical Corporation, 230 Marcus Blvd., Hauppage, N.Y. 11787. In general, Lubrajels can be described as hydrates or clathrates which are formed by the reaction of sodium glycerate with a methacrylic acid polymer. Thereafter, the hydrate or clathrate is stabilized with a small amount of propylene glycol, followed by controlled hydration of the resulting product. Lubrajels are marketed in a number of grades of varying glycerate: polymer ratio and viscosity. Suitable Lubrajels include Lubrajel TW, Lubrajel CG and Lubrajel MS, Lubrajel WA, Lubrajel DV and so-called Lubrajel Oil.

At least part (up to about 5% by weight of composition) of the humectant can be incorporated in the form of an admixture with a particulate lipophilic or hydrophobic carrier material. The carrier material and humectant can be added either to the aqueous or disperse phase.

This copolymer is particularly valuable for reducing shine and controlling oil while helping to provide effective moisturization benefits. The cross-linked hydrophobic polymer is preferably in the form of a copolymer lattice with at least one active ingredient dispersed uniformly throughout and entrapped within the copolymer lattice. Alternatively, the hydrophobic polymer can take the form of a porous particle having a surface area ($N_2$.BET) in the range from about 50 to 500, preferably 100 to 300 $m^2 g^{-1}$ and having the active ingredient absorbed therein.

The cross-linked hydrophobic polymer is preferably present in an amount of from about 0.1% to about 10% by weight and is preferably incorporated in the external aqueous phase. The active ingredient can be one or more or a mixture of skin compatible oils, skin compatible humectants, emollients, moisturizing agents and sunscreens. In one embodiment, the polymer material is in the form of a powder, the powder being a combined system of particles. The system of powder particles forms a lattice which includes unit particles of less than about one micron in average diameter, agglomerates of fused unit particles of sized in the range of about 20 to 100 microns in average diameter and aggregates of clusters of fused agglomerates of sizes in the range of about 200 to 1,200 microns in average diameter.

The powder material of this embodiment can be broadly described as a cross-linked "post absorbed" hydrophobic polymer lattice. The powder preferably has entrapped and dispersed therein, an active which may be in the form of a solid, liquid or gas. The lattice is in particulate form and constitutes free flowing discrete solid particles when loaded with the active material. The lattice may contain a predetermined quantity of the active material. A suitable polymer has the structural formula:

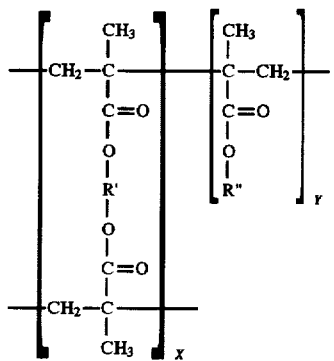

where the ratio of x to y is 80:20, R' is —$CH_2CH_2$— and R" is —$(CH_2)_{11}CH_3$.

The hydrophobic polymer is a highly crosslinked polymer, more particularly a highly cross-linked polymethacrylate copolymer. The material is manufactured by the Dow Corning Corporation, Midland. Michigan, USA, and sold under the trademark POLYTRAP (RTM). It is an ultralight free-flowing white powder and the particles are capable of absorbing high levels of lipophilic liquids and some hydrophilic liquids while at the same time maintaining a free-flowing powder character. The powder structure consists of a lattice of unit particles less than one micron that are fused into agglomerates of 20 to 100 microns and the agglomerates are loosely clustered into macro-particles or aggregates of about 200 to about 1200 micron size. The polymer powder is capable of containing as much as four times its weight of fluids, emulsions, dispersion or melted solids.

Adsorption of actives onto the polymer powder can be accomplished using a stainless steel mixing bowl and a spoon, wherein the active is added to the powder and the spoon is used to gently fold the active into the polymer powder. Low viscosity fluids may be adsorbed by addition of the fluids to a sealable vessel containing the polymer and then tumbling the materials until a consistency is achieved. More elaborate blending equipment such as ribbon or twin cone blenders can also be employed. The preferred active ingredient for use herein is glycerine. Preferably, the weight ratio of humectant: carrier is from about 1:4 to about 3:1.

Also suitable as a highly cross-linked polymethacrylate copolymer is Microsponges 5647. This takes the form of generally spherical particles of cross-linked hydrophobic polymer having a pore size of from about 0.01 to about 0.05 μm and a surface area of 200–300 $m^2/g$. Again, it is preferably loaded with humectant in the levels described above.

The compositions of the invention can also contain a hydrophilic gelling agent at a level preferably from about 0.01% to about 10%, more preferably from about 0.02% to about 2%, and especially from about 0.02% to about 0.5%. The gelling agent preferably has a viscosity (1% aqueous solution, 20° C., Brookfield RVT) of at least about 4000 mPa.s, more preferably at least about 10,000 mPa.s and especially at least 50,000 mPa.s.

Suitable hydrophilic gelling agents can generally be described as water-soluble or colloidally water-soluble polymers, and include cellulose ethers (e.g. hydroxyethyl cellulose, methyl cellulose, hydroxypropylmethyl cellulose), polyvinylpyrrolidone, polyvinylalcohol, guar gum, hydroxypropyl guar gum and xanthan gum.

Preferred hydrophilic gelling agents herein, however, are acrylic acid/ethyl acrylate copolymers and the carboxyvinyl polymers sold by the B. F. Goodrich Company under the trade mark of Carbopol resins. These resins consist essentially of a colloidally water-soluble polyalkenyl polyether crosslinked polymer of acrylic acid crosslinked with from 0.75% to 2.00% of a crosslinking agent such as for example polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. A most preferred polymer is Carbopol 951. Also suitable for use herein are hydrophobically-modified cross-linked polymers of acrylic acid having amphipathic properties available under the Trade Name Carbopol 1382, Carbopol 1342 and Pemulen TR-1 (CTFA Designation: Acrylates/10–30 Alkyl Acrylate Crosspolymer). A combination of the polyalkenyl polyether cross-linked acrylic acid polymer and the hydrophobically modified cross-linked acrylic acid polymer is also suitable and is preferred for use herein. The gelling agents herein are particularly valuable for providing excellent stability characteristics over both normal and elevated temperatures.

Neutralizing agents suitable for use in neutralizing acidic group containing hydrophilic gelling agents herein include sodium hydroxide, potassium hydroxide, ammonium hydroxide, monoethanolamine, diethanolamine and triethanolamine.

The compositions of the invention are in emulsion form and are preferably formulated so as to have a product viscosity of at least about 4,000 mPa.s and preferably in the range from about 4,000 to about 300,000 mPa.s, more preferably from about 8,000 to about 200,000 mPa.s and especially from about 10,000 to about 50,000 mPa.s (250° C., neat, Brookfield RVT Spindle No. 5).

The compositions of the invention can also contain from about 0.1% to about 10%, preferably from about 1% to about 5% of a panthenol moisturizer. The panthenol moisturizer can be selected from D-panthenol ([R]-2,4-dihydroxy-N-[3-hydroxypropyl)]-3,3-dimethylbutamide), DL-panthenol, calcium pantothenate, royal jelly, panthetine, pantotheine, panthenyl ethyl ether, pangamic acid, pyridoxin, pantoyl lactose and Vitamin B complex. Highly preferred from the viewpoint of skin care and tack reduction is D-panthenol.

The compositions of the present invention can additionally comprise from about 0.001% to about 0.5%, preferably from about 0.002% to about 0.05%, more preferably from about 0.005% to about 0.02% by weight of carboxymethylchitin. Chitin is a polysaccharide which is present in the integument of lobsters and crabs and is a mucopolysaccharide having beta (1–4) linkages of N-acetyl-D-glucosamine. Carboxymethylchitin is prepared by treating the purified chitin material with alkali followed by monochloracetic acid. It is sold commercially in the form of a dilute (approximately 0.1% to 0.5% by weight) aqueous solution under the name Chitin Liquid available from A & E Connock Ltd., Fordingbridge, Hampshire, England.

Other optional materials include keratolytic agents such as salicylic acid; proteins and polypeptides and derivatives thereof; water-soluble or solubilizable preservatives such as Germall 115, methyl, ethyl, propyl and butyl esters of hydroxybenzoic acid, benzyl alcohol, EDTA, Euxyl (RTM) K400, Bromopol (2-bromo-2-nitropropane-1,3-diol) and phenoxypropanol; anti-bacterials such as Irgasan (RTM) and phenoxyethanol (preferably at levels of from 0.1% to about 5%); soluble or colloidally-soluble moisturising agents such as hylaronic acid and starch-grafted sodium polyacrylates such as Sanwet (RTM) IM-1000, IM-1500 and IM-2500 available from Celanese Superabsorbent Materials, Portsmith, Va., USA and described in U.S. Pat. No. 4,076, 663; colouring agents; perfumes and perfume solubilizers and additional surfactants/emulsifiers such as fatty alcohol ethoxylates, ethoxylated polyol fatty acid esters, wherein the polyol can be selected from glycerine, propyleneglycol, ethyleneglycol, sorbitol, sorbitan, polypropyleneglycol, glucose and sucrose. Examples include glyceryl monohydroxy stearate and stearyl alcohol ethoxylated with an average of from 10 to 200 moles of ethyleneoxide per mole of alcohol and PEG-6 caprylic/capric glycerides.

Preferred embodiments of the invention additionally comprise from about 0.1% to about 5% by weight of aluminium starch octenylsuccinate. Aluminium starch octenylsuccinate is the aluminium salt of the reaction product of octenylsuccinic anhydride with starch and is commercially available under the trade name from Dry Flo National Starch & Chemical Ltd. Dry Flo is useful herein from the viewpoint of skin feel and application characteristics.

Other optional materials herein include pigments. Pigments suitable for use in the compositions of the present invention can be organic and/or inorganic. Also included within the term pigment are materials having a low colour or lustre such as matte finishing agents, and also light scattering agents. Examples of suitable pigments are iron oxides, acyglutamate iron oxides, ultramarine blue, D&C dyes, carmine, and mixtures thereof. Depending upon the type of composition, a mixture of pigments will normally be used. The preferred pigments for use herein from the viewpoint of moisturisation, skin feel, skin appearance and emulsion compatibility are treated pigments. The pigments can be treated with compounds wuch as amino acids, silicones, lecithin and ester oils.

The pH of the compositions is preferably from about 4 to about 9, more preferably from about 5 to about 7.5.

The invention is illustrated by the following examples

EXAMPLES I to V

|  | I | II | III | IV | V |
|---|---|---|---|---|---|
| Cetyl Alcohol | 0.25 | 0.3 | 0.2 | 0.3 | 0.25 |
| Stearic Acid | 0.11 | 0.2 | 0.1 | 0.2 | 0.1 |
| Steareth 100 | 0.1 | 0.1 | 0.15 | 0.15 | 0.15 |
| GMHS (1) | 0.15 | 0.2 | 0.1 | 0.2 | 0.15 |
| Cetyl Palmitate | 3.0 | 2 | 3 | 4 | 2.5 |
| Mineral Oil | 2.0 | 3 | 4 | 3 | 3.5 |
| Petrolatum | 3.00 | 2 | 2.5 | 4 | 3.5 |
| Wickenol 142 (RTM) | 0.60 | 1 | 1 | 1 | 0.7 |
| Dimethicone 200 | 0.3 | 0.4 | 0.5 | 0.5 | 0.4 |
| Propyl Paraben | 0.08 | 0.08 | 0.07 | 0.08 | 0.07 |
| Arlatone (RTM) 2121 | 6 | 4 | 7 | 5 | 4 |
| Glycerin | 3 | 3 | 3 | 2 | 3 |
| Carbopol (RTM) 1342 | 0.095 | 0.075 | 0.075 | 0.075 | 0.075 |
| Carbopol (RTM) 951 | 0.09 | 0.08 | 0.09 | 0.09 | 0.08 |
| Na4 EDTA | 0.1 | 0.2 | 0.1 | 0.1 | 0.1 |
| Methyl Paraben | 0.175 | 0.175 | 0.175 | 0.175 | 0.175 |
| KOH | 0.3 | 0.2 | 0.2 | 0.2 | 0.2 |
| Dimethicone Q21403 | 3 | — | 4 | 3 | — |
| CeRiccinoleate | — | 2 | — | 1 | — |
| Butylene Glycol | — | — | — | 2 | — |
| DryFlo (RTM) | — | 1 | — | 0.5 | — |
| Perfume | 0.2 | 0.2 | — | 0.2 | — |
| Colour | 0.0004 | 0.0002 | 0.0003 | — | — |

(1) Glycerylmonohydroxystearate

The compositions are made as follows:

A first premix of thickening agents, Arlatone 2121 and other water soluble ingredients is prepared by admixing in water and heating. A second premix of oil phase ingredients other than silicone gum is prepared by mixing and heating and is added to the aqueous premix.

The resulting mixture is cooled. The silicone gum is then added to the resulting oil-in-water emulsion and the mixture is cooled before adding minor ingredients. The composition is ready for packaging.

The compositions display improved moisturisation, skin feel and skin care characteristics together with reduced greasiness and excellent rub-in and absorption characteristics.

EXAMPLES VI to X

|  | VI | VII | VIII | IX | X |
|---|---|---|---|---|---|
| Cetyl Alcohol | 0.25 | 0.3 | 0.2 | 0.3 | 0.25 |
| Stearic Acid | 0.11 | 0.2 | 0.1 | 0.2 | 0.1 |
| Steareth 100 | 0.1 | 0.1 | 0.15 | 0.15 | 0.15 |
| GMHS (1) | 0.15 | 0.2 | 0.1 | 0.2 | 0.15 |
| Cetyl Palmitate | 3.0 | 2 | 3 | 4 | 2.5 |
| Mineral Oil | 2.0 | 3 | 4 | 3 | 3.5 |
| Petrolatum | 3.00 | 2 | 2.5 | 4 | 3.5 |
| Wickenol 142 (RTM) | 0.60 | 1 | 1 | 1 | 0.7 |
| Dimethicone 200 | 0.3 | 0.4 | 0.5 | 0.5 | 0.4 |
| Propyl Paraben | 0.08 | 0.08 | 0.07 | 0.08 | 0.07 |
| Arlatone (RTM) 2121 | 6 | 4 | 7 | 5 | 4 |
| Glycerin | 3 | 3 | 1.5 | 2 | 3 |
| Carbopol (RTM) 1342 | 0.095 | 0.075 | 0.075 | 0.075 | 0.075 |
| Carbopol (RTM) 951 | 0.09 | 0.08 | 0.09 | 0.09 | 0.08 |
| Na4 EDTA | 0.1 | 0.2 | 0.1 | 0.1 | 0.1 |
| Methyl Paraben | 0.175 | 0.175 | 0.175 | 0.175 | 0.175 |
| KOH | 0.3 | 0.2 | 0.2 | 0.2 | 0.2 |
| Dimethicone Q21403 | 3 | — | 4 | 3 | — |
| Cyclomethicone/ dimethicone copolyol | 1.0 | 1.0 | — | 1.0 | 1.0 |
| Microsponges 5647 | — | — | 3.0 | — | — |
| Lecithin | — | 0.1 | — | — | — |
| Phenoxyethanol | 0.2 | 0.2 | 0.2 | 0.2 | 0.2 |

-continued

|  | VI | VII | VIII | IX | X |
|---|---|---|---|---|---|
| CeRiccinoleate | — | 2 | — | 1 | — |
| Butylene Glycol | — | — | — | 2 | — |
| DryFlo (RTM) | — | 1 | — | 0.5 | — |
| Perfume | 0.2 | 0.2 | — | 0.2 | — |
| Colour | 0.0004 | 0.0002 | 0.0003 | — | — |

(1) Glycerylmonohydroxystearate

The compositions of Examples VI to X are made in the same way as the compositions of Examples I–V above.

We claim:

1. A skin care composition in the form of an oil-in-water dispersion comprising:

a) from about 1% to about 20% by weight of a silicone or mixture of silicones wherein the silicone or mixture of silicones comprises a silicone gum having a molecular weight of from about 200,000 to about 4,000,000;

b) from about 0.1% to about 5% by weight of aluminum starch octenylsuccinate; and c) from about 2% to about 10% by weight of an emulsifier capable of forming liquid crystals in water, the emulsifier being a fatty acid ester blend comprising a mixture of sorbitan fatty acid ester and sucrose fatty acid ester.

2. A skin care composition in the form of an oil-in-water dispersion comprising:

a) from about 1% to about 20% by weight of a silicone or mixture of silicones wherein the silicone or mixture of silicones comprises a silicone gum having a molecular weight of from about 200,000 to about 4,000,000;

b) from about 0.1% to about 10% by weight of a hydrophilic gelling agent selected from colloidally water-soluble polymers of acrylic acid cross-linked with from about 0.75% to about 2% of a cross-linked agent selected from polyalkyl sucrose and polyalkyl pentaerythritol; and c) from about 2% to about 10% by weight of an emulsifier capable of forming liquid crystals in water, the emulsifier being a fatty acid ester blend comprising a mixture of sorbitan fatty acid ester and sucrose fatty acid ester.

* * * * *